United States Patent
Kazmi et al.

(10) Patent No.: US 11,547,690 B1
(45) Date of Patent: Jan. 10, 2023

(54) CHEMOTHERAPEUTIC SELF-NANOEMULSIFYING DRUG DELIVERY SYSTEMS AND USES THEREOF

(71) Applicant: KING ABDULAZIZ UNIVERSITY, Jeddah (SA)

(72) Inventors: Imran Kazmi, Jeddah (SA); Sarwar Beg, Jeddah (SA); Mahroozur Rahman, Jeddah (SA); Fahad A. Al-Abbasi, Jeddah (SA); Muhammad Afzal, Jeddah (SA); Hisham N. Altayeb, Jeddah (SA)

(73) Assignee: KING ABDULAZIZ UNIVERSITY, Jeddah (SA)

( * ) Notice: Subject to any disclaimer, the term of this patent is extended or adjusted under 35 U.S.C. 154(b) by 0 days.

(21) Appl. No.: 17/851,399

(22) Filed: Jun. 28, 2022

(51) Int. Cl.
| | |
|---|---|
| *A61K 31/337* | (2006.01) |
| *A61K 31/4725* | (2006.01) |
| *A61K 31/235* | (2006.01) |
| *A61K 9/107* | (2006.01) |
| *A61K 47/14* | (2017.01) |
| *A61K 47/10* | (2017.01) |
| *A61P 35/00* | (2006.01) |
| *A61K 47/42* | (2017.01) |

(52) U.S. Cl.
CPC .......... *A61K 31/337* (2013.01); *A61K 9/1075* (2013.01); *A61K 31/235* (2013.01); *A61K 31/4725* (2013.01); *A61K 47/10* (2013.01); *A61K 47/14* (2013.01); *A61K 47/42* (2013.01); *A61P 35/00* (2018.01)

(58) Field of Classification Search
None
See application file for complete search history.

(56) References Cited

U.S. PATENT DOCUMENTS

| | | | |
|---|---|---|---|
| 8,128,905 B2 | 3/2012 | Anderson | |
| 9,220,680 B2 | 12/2015 | Perumal et al. | |
| 2021/0046019 A1* | 2/2021 | Hekimi | A61K 9/08 |

OTHER PUBLICATIONS

Sandhu et al., Expert Opinion on Drug Delivery (2015), 12:11, pp. 1809-1822.*
Harshita et al., AAPS PharmSciTech (2019) 20:87, 14 pages.*
Ohadi et al., Drug Design, Developementand Therapy (2020), 14, pp. 541-550.*
Abdallah et al: "Utilization of novel self-nanoemulsifying formulations (SNEFs) loaded paclitaxel for the treatment prosperity of bladder cancer", Journal of Drug Delivery Science and Technology, vol. 56, Jan. 10, 2020.
Ahmad et al: "Quality by Design Approach for Self Nanoemulsifying System of Paclitaxel", Science of Advanced Materials, vol. 6, No. p. 1778-1791, Aug. 2014, (abstract).
Cevc et al: Transfersomes' mediated transepidermal delivery improves the regiospecificity and biological activity of corticosteroids in vivo', Journal of Controlled Release, vol. 45, p. 211-226, 1997.
Dinshaw et al: "Nanoemulsions: A Review on the Conceptualization of Treatment for Psoriasis Using a 'Green' Surfactant with Low-Energy Emulsification Method", Pharmaceutics, vol. 13, 2021.
Utreja et al: "Localized delivery of paclitaxel using elastic liposomes: Formulation development and evaluation", Drug Delivery, vol. 18, No. 5, p. 367-376, 2011.

* cited by examiner

*Primary Examiner* — Brian J Davis
(74) *Attorney, Agent, or Firm* — WCF IP

(57) ABSTRACT

Self-nanoemulsifying drug delivery system (SNEDDS) composition are provided. The compositions include at least one chemotherapeutic compound or a pharmaceutically acceptable salt thereof or mixture thereof, at least one biocompatible surfactant, wherein the at least one biocompatible surfactant includes surfactin, and at least one co-surfactant. Methods of enhancing the bioavailability of the chemotherapeutic compound and for treating cancer are also provided.

10 Claims, 7 Drawing Sheets

FIG. 9A
FIG. 9B
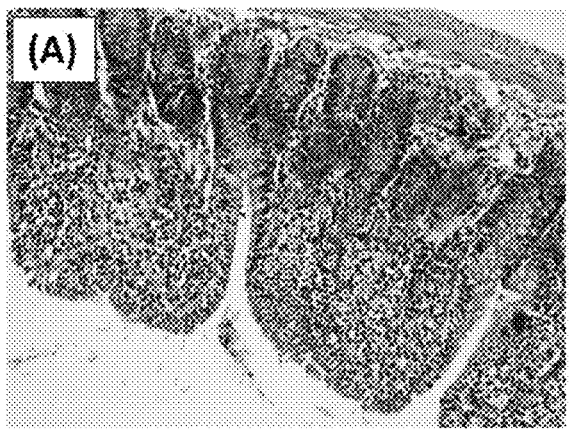
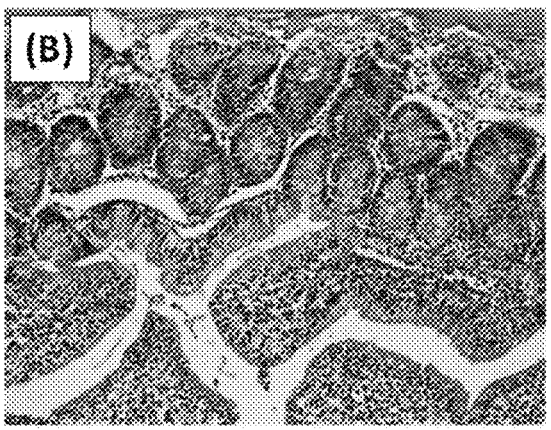
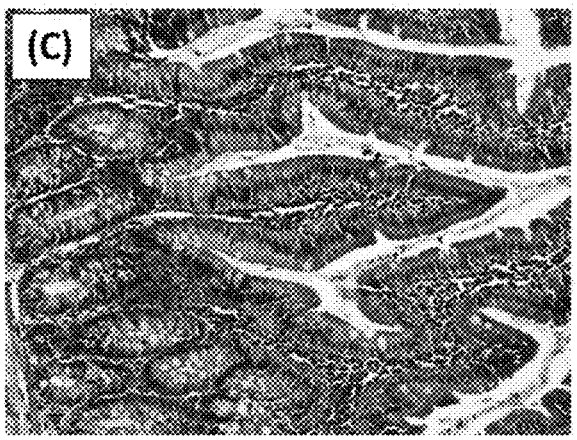
FIG. 9C

CHEMOTHERAPEUTIC SELF-NANOEMULSIFYING DRUG DELIVERY SYSTEMS AND USES THEREOF

FIELD OF THE INVENTION

The invention relates to self-nanoemulsifying formulations that enhance the bioavailability of chemotherapeutic agents.

BACKGROUND OF THE INVENTION

For more than a decade, several research studies have been conducted for oral delivery of anticancer drugs in order to increase the patient compliance over the parenteral route of drug administration [1]. Beyond the advantages such as low cost drug therapy and noninvasive route of administration for oral drug therapy, it primarily suffers from challenges like low and inconsistent bioavailability of drugs due to poor solubility and permeability, hepatic first-pass effect, metabolism by gastrointestinal enzymes and instability under acidic conditions [2]. Thus, novel oral formulations for effective delivery of the drugs are urgently needed which can reduce the challenges associated with the oral delivery of anticancer drugs. These include nanostructured formulations of the drugs which improve the bioavailability and anticancer activity of the drugs [3, 4].

Paclitaxel is a derivative of taxane used for its potent anticancer activity over the past three decades. However, it exhibits very low oral bioavailability (5%) due to its practically insoluble nature along with minimal intestinal permeability and efflux by P-gp transporters [5]. In order to overcome these challenges, several researchers have already explored the worth of using a variety of nanoformulations for paclitaxel delivery and a score of success is available in this domain [6-11], especially the albumin-based nanoparticles and similar products are available on the market, as described in the literature elsewhere [12, 13]. Although such formulations have gained immense popularity despite high manufacturing challenges and cost of drug therapy, yet there has been a continuous surge for developing more effective, efficient and cost-efficient therapeutic products.

SUMMARY

The disclosure provides nanoformulations comprising biosurfactants derived from microbial origin as opposed to synthetic surfactants for improving the safety and efficacy of chemotherapy for the treatment of cancer. The disclosed compositions and methods provide synergistic therapeutic benefits to taxane therapy due to the anticancer activity of the microbial bio surfactants.

One aspect of the disclosure provides a self-nanoemulsifying drug delivery system (SNEDDS) composition comprising at least one chemotherapeutic compound, wherein the at least one chemotherapeutic compound is selected from the group consisting of abeotaxane, paclitaxel, oraxol, and docetaxel or a pharmaceutically acceptable salt thereof or mixture thereof, at least one biocompatible surfactant, wherein the at least one biocompatible surfactant includes surfactin, and at least one co-surfactant. In some embodiments, the composition comprises 45-65 wt % surfactin. In some embodiments, the at least one co-surfactant is selected from the group consisting of ethyl oleate, polyglyceryl-3 dioleate, and 2-(2-ethoxyethoxy)ethanol. In some embodiments, the co-surfactant includes 1-10 wt % ethyl oleate, 1-10 wt % polyglyceryl-3 dioleate, and 30-40 wt % 2-(2-ethoxyethoxy)ethanol. In some embodiments, the at least one co-surfactant includes ethyl oleate and polyglyceryl-3 dioleate at a 1:1 molar ratio. In some embodiments, the composition does not contain polyethoxylated castor oil. In some embodiments, the composition does not contain polyoxyethylene sorbitan monooleate.

Another aspect of the disclosure provides a method of enhancing the bioavailability of a chemotherapeutic compound in a subject, comprising orally administering an effective amount of a composition as described herein to the subject.

Another aspect of the disclosure provides a method of treating cancer in a subject in need thereof, comprising administering an effective amount of a composition as described herein to the subject.

Additional features and advantages of the present invention will be set forth in the description of disclosure that follows, and in part will be apparent from the description of may be learned by practice of the disclosure. The disclosure will be realized and attained by the compositions and methods particularly pointed out in the written description and claims hereof.

BRIEF DESCRIPTION OF THE DRAWINGS

FIGS. 9A-C. Histopathology images of the excised rat intestine stained with eosin and hematoxylin, (A) Control intestine, and intestine treated with (B) Surfactin SNEDDS and (C) Tween® 80 SNEDDS.

DETAILED DESCRIPTION

Figure 1A:
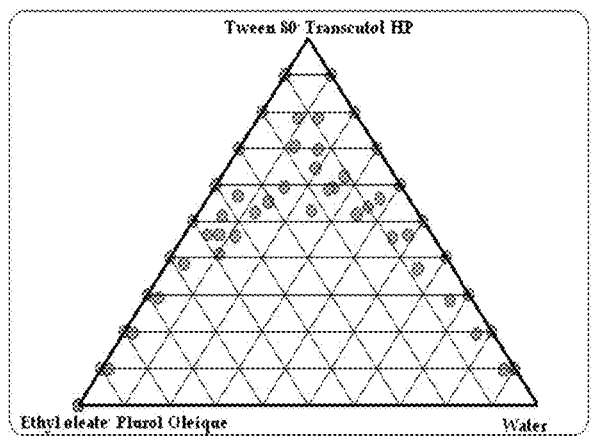
FIG. 1A-B. Pseudoternary phase diagram for SNEDDS prepared using (A) Tween® 80 and (B) Surfactin.

Embodiments of the disclosure provide nanoformulations containing chemotherapeutic agents. The compositions allow for the reduction in the dose of drug which can reduce the toxicity and side-effects. In addition, the compositions achieve more specific targeting of drug to cancer cells due to the presence of a microbial surfactant having anticancer activity. An advantage of using a microbial surfactant as compared to synthetic surfactants is less gastric irritation and toxicity due to high biocompatibility.

Provided herein are pharmaceutical compositions comprising one or more taxanes (a class of diterpenes), such as one or more of abeotaxane, paclitaxel, oraxol, and docetaxel or pharmaceutically acceptable salts thereof. Such compositions may take various forms such as liquid-filled capsules, syrups, and a self-emulsifying formulation, such as a self-emulsifying drug delivery system (SEDDS), self-microemulsifying drug delivery system (SMEDDS), and self-nanoemulsifying drug delivery systems (SNEDDS). SEDDS, SMEDDS, and SNEDDS can be differentiated according to their size of globules upon aqueous dispersion. A lipid formulation classification system (LFCS) based on the composition was developed which categorized the LBF into four different types. The LFCS explains the formation of different types of self-emulsifying formulations in a very simple way based on their types and compositions. Briefly, Type I formulations represent 100% pure oil (surfactant free) as component. Types II and IIIA systems contain water insoluble surfactants (HLB <10) with different % oil in the formulation (Type II contain 60-80% oil and Type IIIA contain 40-60% oil). Type IIIB formulations contain water soluble surfactant and oil (20-50% oil), whereas Type IV formulations contain only water soluble surfactant/cosolvent without oil. Nanoemulsion fabrication methods are known in the art and comprise both high-energy and low-energy emulsification methods.

As used herein, the term "self-nanoemulsifying drug delivery system" or "SNEDDS" means anhydrous homogenous liquid mixtures comprising oil, one or more surfactants, drug, and one or more co-emulsifying agents or solubilizers which spontaneously form a nanoemulsion of approximately 20-200 nm (or less than 20 nm) in size upon dilution with water under gentle agitation. Nanoformulations with a particle size of less than 200 nm enhance permeability across the intestine. In some embodiments, the SNEDDS formulations may be filled in soft or hard gelatin capsules. Alternatively, hydroxypropyl methylcellulose (HPMC) capsules (moisture content 3-8%) may be useful for moisture-sensitive and hygroscopic products and whenever capsules of vegetable source need to be used. SNEDDS may be used to improve the solubility and bioavailability of hydrophobic drugs. Nanoemulsion fabrication methods are known in the art and comprise both high-energy and low-energy emulsification methods (Date et al., Nanomedicine (2010) 5(10), 1595-1616).

Oils that may be included in formulations described herein include jojoba oil, castor oil, groundnut oil, pumpkin seed oil, black seed oil, soybean oil, coconut oil, canola oil, safflower oil, olive oil, corn oil, cottonseed oil, linseed oil, safflower oil, palm oil, peanut oil, flaxseed oil, sunflower oil, rice bran oil, sesame oil, rapeseed oil, cocoa butter, almond oil, cashew oil, hazelnut oil, macadamia oil, mongongo nut oil, pecan oil, pine nut oil, pistachio oil, sachainchi oil, walnut oil, bottle gourd oil, buffalo gourd oil, butternut squash seed oil, watermelon seed oil, acai oil, blackcurrant seed oil, borage seed oil, evening primrose oil, carob pod oil, amaranth oil, apricot oil, apricot kernel oil, apple seed oil, argan oil, artichoke oil, avocado oil, babassu oil, ben oil, borneo tallow nut oil, cape chestnut oil, cassia oil, cocoa butter, cocklebur oil, cohune oil, coriander seed oil, dika oil, grape seed oil, hemp oil, kapok seed oil, kenaf seed oil, lallemantia oil, manila oil, meadowfoam seed oil, mustard oil, nutmeg butter, okra seed oil, papaya seed oil, perilla seed oil, pequi oil, poppyseed oil, prune kernel oil, quinoa oil, ramtil oil, royle oil, tea seed oil, thistle oil, tigernut oil, tomato seed oil, wheat germ oil, radish oil, salicornia oil, tung oil, algae oil, copaiba oil, honge oil, jatropha oil, petroleum nut oil, WL 1349 oil, a silicone oil, and a mineral oil.

The formulations described herein also contain a biocompatible surfactant. Biocompatible surfactants are derived from a natural origin such as from animals, plants and microbial sources, and are very effective in low concentration for use in the nanoemulsion formulations. Unlike synthetic surfactants, the biosurfactants have key features like high biocompatibility, better tolerance and absence of toxic effects. "Biocompatibility" refers to a substance which is substantially non-toxic and does not cause a severe adverse biological reaction when administered at reasonable doses and rates. Suitable biosurfactants include surfactin, pumilacidin, iturin, lichenysin, rhamnolipid, glycolipid, etc. In some embodiments, the biosurfactants have biological activity such as antimicrobial, antifungal, antiadhesive, or anticancer activity. Surfactin is a microbial biosurfactant obtained from *Bacillus Subtilis*, which has HLB value of 10-12 (M.W. 1036 Da) and exhibits very powerful activity for reducing surface tension. Beyond this, surfactin also possess a strong anticancer property along with antimicrobial, antiviral and cytolytic activities. In some embodiments, the formulations described herein are prepared with or without synthetic surfactants such as polyethoxylated castor oil (Cremophor® EL, also known as Kolliphor® EL), polysorbates (Tweens® such as polyoxyethylene sorbitan monooleate (Tween® 80)), sorbitan esters of fatty acids (Spans®), Poloxamers®, Gelucires®, Labrafils®, Labrasols®, Maisines®, etc. Synthetic surfactants can result in high gastrointestinal irritation and toxic effects, particularly when given through the oral route. In some embodiments, the composition includes at least one co-surfactant selected from the group consisting of ethyl oleate, polyglyceryl-3 dioleate (Plurol® Oleique), and 2-(2-ethoxyethoxy) ethanol (Transcutol®).

In an embodiment, each surfactant or emulsifying agent is present in the composition from about 1 wt % to about 70 wt %/volume, e.g. about 15-40 wt %. It should be understood that throughout the specification the term weight percent (wt %) refers to mass per unit volume, unless otherwise specified.

In some embodiments, the composition includes about 40-7-wt % surfactin, e.g. about 45-65 wt %, about 50-60 wt %, or about 55 wt % surfactin. In some embodiments, the composition includes about 1-10 wt %, e.g. about 4-6 wt % or about 5 wt % ethyl oleate. In some embodiment, the composition includes about 1-10 wt %, e.g. about 4-6 wt % or about 5 wt % polyglyceryl-3 dioleate. In some embodiments, the composition includes about 30-40 wt %, e.g. about 34-36 wt % or about 35 wt % 2-(2-ethoxyethoxy) ethanol. In some embodiments, ethyl oleate and polyglyceryl-3 dioleate are present in a 1:1 molar ratio.

Additional molecules which may be incorporated in a formulation as described herein include additional anticancer agents, bile acids, anti-hyperlipidemic drugs, antiseizure drugs, and anti-inflammatory drugs.

Exemplary additional anti-cancer agents include but are not limited to: alkylating agents, such as mustard gas derivatives (Mechlorethamine, Cyclophosphamide (Cytoxan), Chlorambucil (Leukeran), Melphalan, and Ifosfamide), ethylenimines (Thiotepa (Thioplex) and Hexamethylmelamine), alkylsulfonates (Busulfan (Myleran)), hydrazines and triazines (Altretamine (Hexalen), Procarbazine (Matulane), Dacarbazine (DTIC) and Temozolomide), nitrosureas (Carmustine, Lomustine and Streptozocin), and metal salts (Carboplatin, Cisplatin (Platinol), and Oxaliplatin), Mechlorethamine, and Melphalan (Alkeran); plant alkaloids, terpenoids and topoisomerase inhibitors, such as vinca alkaloids (Vincristine (Oncovin), Vinblastine (Velban), Vindesine, and Vinorelbine), taxanes (Paclitaxel (Taxol) and Docetaxel (Taxotere)), podophyllotoxins (Etoposide and Tenisopide), and camptothecan analogs (Irinotecan and Topotecan); antitumor antibiotics, such as anthracyclines (Doxorubicin (Adriamycin, Rubex, Doxil), Daunorubicin, Epirubicin, Mitoxantrone, Idarubicin, Duocarmycin, and Dactinomycin (Cosmegen)), chromomycins (Dactinomycin and Plicamycin (Mithramycin)), and miscellaneous (Mitomycin and Bleomycin (Blenoxane)); antimetabolites, such as folic acid antagonists (Methotrexate), pyrimidine antagonists (5-Fluorouracil, Foxuridine, Cytarabine, Flurouracil (5-FU), Capecitabine, and Gemcitabine), purine antagonists (6-Mercaptopurine (Purinethol) and 6-Thioguanine), 6-Thiopurines, and adenosine deaminase inhibitor (Cladribine (Leustatin), Fludarabine, Nelarabine and Pentostatin), Azacitidine, Thioguanine, and Cytarabine (ara-C); topoisomerase Inhibitors, such as topoisomerase I inhibitors (Ironotecan, topotecan), and topoisomerase II inhibitors (Amsacrine, etoposide, etoposide phosphate, teniposide); hormonal agents, exemplified by Estrogen and Androgen Inhibitors (Tamoxifen and Flutamide), Gonadotropin-Releasing Hormone Agonists (Leuprolide and Goserelin (Zoladex)), Aromatase Inhibitors (Aminoglutethimide and Anastrozole (Arimidex)); DNA hypomethylating agents, e.g., Azacitidine, Decitabine; Poly(adenosine diphosphate [ADP]-ribose) polymerase (PARP) pathway inhibitors, such as Iniparib, Olaparib, Veliparib; PI3K/Akt/mTOR pathway inhibitors, e.g., Everolimus; Histone deacetylase (HDAC) inhibitors, e.g., Vorinostat, Entinostat (SNDX-275), Mocetinostat (MGCD0103), Panobinostat (LBH589), Romidepsin, Valproic acid; Cyclin-dependent kinase (CDK) inhibitors, e.g., Flavopiridol, Olomoucine, Roscovitine, Kenpaullone, AG-024322 (Pfizer), Fascaplysin, Ryuvidine, Purvalanol A, NU2058, BML-259, SU 9516, PD-0332991, P276-00; Heat shock protein (HSP90) inhibitors, e.g., Geldanamycin, Tanespimycin, Alvespimycin, Radicicol, Deguelin, and BIIB021; Murine double minute 2 (MDM2) inhibitors, e.g., Cis-imidazoline, Benzodiazepinedione, Spiro-oxindoles, Isoquinolinone, Thiophene, 5-Deazaflavin, Tryptamine; Anaplastic lymphoma kinase (ALK) inhibitors, e.g., Aminopyridine, Diaminopyrimidine, Pyridoisoquinoline, Pyrrolopyrazole, Indolocarbazole, Pyrrolopyrimidine, Dianilinopyrimidine; Poly [ADPribose] polymerase (PARP) inhibitors, illustrated by Benzamide, Phthalazinone, Tricyclic indole, Benzimidazole, Indazole, Pyrrolocarbazole, Phthalazinone, Isoindolinone; and miscellaneous anticancer drugs, exemplified by Amsacrine, Asparaginase (El-spar), Hydroxyurea, Mitoxantrone (Novantrone), Mitotane (Lysodren), Maytansinoid, Retinoic acid Derivatives, Bone Marrow Growth Factors (sargramostim and filgrastim), Amifostine, agents disrupting folate metabolism, e.g., Pemetrexed, ribonucleotide reductase inhibitors (Hydroxyurea), adrenocortical steroid inhibitors (Mitotane), enzymes (Asparaginase and Pegaspargase), antimicrotubule agents (Estramustine), and retinoids (Bexarotene, Isotretinoin, Tretinoin (ATRA)).

Chemotherapy drugs that are illustrative of the small molecule drug subcategory are Actinomycin-D, Alkeran, Ara-C, Anastrozole, BiCNU, Bicalutamide, Bleomycin, Busulfan, Capecitabine, Carboplatin, Carboplatinum, Carmustine, CCNU, Chlorambucil, Cisplatin, Cladribine, CPT-11, Cyclophosphamide, Cytarabine, Cytosine arabinoside, Cytoxan, Dacarbazine, Dactinomycin, Daunorubicin, Dexrazoxane, Docetaxel, Doxorubicin, DTIC, Epirubicin, Ethyleneimine, Etoposide, Floxuridine, Fludarabine, Fluorouracil, Flutamide, Fotemustine, Gemcitabine, Hexamethylamine, Hydroxyurea, Idarubicin, Ifosfamide, Irinotecan, Lomustine, Mechlorethamine, Melphalan, Mercaptopurine, Methotrexate, Mitomycin, Mitotane, Mitoxantrone, Oxaliplatin, Paclitaxel, Pamidronate, Pentostatin, Plicamycin, Procarbazine, Steroids, Streptozocin, STI-571, Streptozocin, Tamoxifen, Temozolomide, Teniposide, Tetrazine, Thioguanine, Thiotepa, Tomudex, Topotecan, Treosulphan, Trimetrexate, Vinblastine, Vincristine, Vindesine, Vinorelbine, VP-16, and Xeloda.

The subcategory of biologic chemotherapy drugs includes, without limitation, Asparaginase, AIN-457, Bapineuzumab, Belimumab, Brentuximab, Briakinumab, Canakinumab, Cetuximab, Dalotuzumab, Denosumab, Epratuzumab, Estafenatox, Farletuzumab, Figitumumab, Galiximab, Gemtuzumab, Girentuximab (WX-G250), Herceptin, Ibritumomab, Inotuzumab, Ipilimumab, Mepolizumab, Muromonab-CD3, Naptumomab, Necitumumab, Nimotuzumab, Ocrelizumab, Ofatumumab, Otelixizumab, Ozogamicin, Pagibaximab, Panitumumab, Pertuzumab, Ramucirumab, Reslizumab, Rituximab, REGN88, Solanezumab, Tanezumab, Teplizumab, Tiuxetan, Tositumomab, Trastuzumab, Tremelimumab, Vedolizumab, Zalutumumab, and Zanolimumab.

In some embodiments, the compositions described herein may be incorporated into another pharmaceutically acceptable carrier in a form suitable for therapeutic delivery to a subject. Another carrier or suspension for injections includes sterile saline, bacteriostatic water, phosphate buffered saline (PBS), ethanol or polyol (for example, glycerol, propylene glycol and polyethylene glycol and the like). The term "pharmaceutically acceptable carrier" as used herein refers to any and all solvents, dispersion media, coatings, isotonic and absorption delaying agents, and the like, that are compatible with pharmaceutical administration. The compositions may also contain other active compounds providing supplemental, additional, or enhanced therapeutic functions.

In some embodiments, the compositions described herein are useful for the same indications as the chemotherapeutic agent per se. In some embodiments, the disclosure provides a method for treating cancer in a subject in need thereof, the method comprising administering to the subject an effective amount of a composition as described herein. The cancer to be treated may be any cancer suitable for treatment with the chemotherapeutic agent, including, for example, breast cancer, prostate cancer, ovarian cancer, skin cancer, lung cancer, gastrointestinal cancer, colon cancer, brain cancer, pancreatic cancer, leukemia, etc.

Further embodiments provide a method for increasing bioavailability of a drug, such as a chemotherapeutic agent, in a subject in need thereof, the method comprising orally administering a composition as described herein to the subject.

In some embodiments, the compositions are administered in a dosage ranging from about 0.001 to about 500 mg/kg of subject body weight including any and all ranges and subranges therein (e.g., 0.001 to 100 mg/kg, 0.01 to 75 mg/kg, 0.05 to 20 mg/kg, 0.1 to 10 mg/kg, etc.).

In some embodiments, the compositions are administered in an amount of 1 to 2,000 mg including any and all ranges and subranges therein (e.g., 1-10 mg, 20 to 1900 mg, 50 to 1800 mg, 75 to 1700 mg, 100 to 1600 mg, etc.).

In some aspects, the compositions are administered simultaneously, separately, or sequentially with one or more therapeutic agents such as a cardiovascular, anti-inflammatory, anti-diabetic, or an additional anti-cancer agent, such as another chemotherapeutic agent, radiotherapy, or immunotherapy.

The compositions described herein may be used to deliver other poorly water-soluble drugs. As used herein, the term "poorly water-soluble" or "lipophilic" refers to having a solubility in water at 20° C. of less than 1%, e.g., 0.01% (w/v), i.e., a "sparingly soluble to very slightly soluble drug" as described in Remington, *The Science and Practice of Pharmacy*, 19$^{th}$ Edition, A. R. Gennaro, Ed., Mack Publishing Company, Vol. 1, p. 195 (1995). Examples of therapeutic classes of therapeutic compounds include, but are not limited to, antihypertensives, antianxiety agents, anticlotting agents, anticonvulsants, blood glucose-lowering agents, decongestants, antihistamines, antitussives, antineoplastics, beta (β)-blockers, anti-inflammatories, antipsychotic agents, cognitive enhancers, anti-atherosclerotic agents, cholesterol reducing agents, anti-obesity agents, autoimmune disorder agents, anti-impotence agents, antibacterial and antifungal agents, hypnotic agents, antibiotics, anti-depressants, anti-Parkinsonism agents, anti-Alzheimer's disease agents, antiviral agents and combinations of the foregoing.

The compositions of the disclosure may be administered orally. Formulations suitable for oral administration include solid formulations, such as tablets, capsules containing particulates, liquids, or powders; lozenges (including liquid-filled), chews; multi- and nano-particulates; gels, solid solution, liposome, films (including muco-adhesive), ovules, sprays and liquid formulations. The pharmaceutical composition may, for example, be in a form suitable for oral administration as a tablet, capsule, pill, powder, sustained release formulations, solution, or suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier and a compound according to the invention as an active ingredient. In addition, it may include other medicinal or pharmaceutical agents, carriers, adjuvants, etc.

The relative amounts of the active ingredient, the pharmaceutically acceptable carrier, and any additional ingredients in a pharmaceutical composition will vary, depending upon the identity, size, and condition of the subject treated and further depending upon the route by which the composition is to be administered. By way of example, the composition may comprise between 0.1% and 100% (w/w) active ingredient.

An effective amount of a composition sufficient to achieve a therapeutic or prophylactic effect should be determined by standard procedures used by medical professionals, e.g. physicians. The compositions described herein may be administered on multiple occasions. The interval between single doses can be daily, weekly, monthly, or yearly. Alternatively, the composition can be administered as a sustained release formulation. As noted above, dosage and frequency will vary depending on a plurality of considerations including the intended uses (i.e. prevention or treatment), efficacy and the half-life of the composition in a subject.

By a "therapeutically effective amount" is meant a sufficient amount of active agent to treat the disease or disorder at a reasonable benefit/risk ratio applicable to any medical treatment. It will be understood that the total daily usage of the compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidental with the specific active agent employed; and like factors well known in the medical arts. For example, it is well within the skill of the art to start doses of the compound at levels or frequencies lower than those required to achieve the desired therapeutic effect and to gradually increase the dosage or frequency until the desired effect is achieved. However, the daily dosage of the active agent may be varied over a wide range from 0.01 to 1,000 mg per adult per day. In particular, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, in particular, from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 10 mg/kg of body weight per day.

The active agent may be combined with pharmaceutically acceptable excipients. "Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type. The compounds described herein are generally delivered (administered) in a pharmaceutical composition and the present disclosure encompasses such formulations/compositions. The pharmaceutical compositions generally comprise at least one of the disclosed compounds, i.e. one or more than one (a plurality of) different compounds in a single formulation. The compositions also generally include a pharmacologically suitable (physiologically compatible) carrier, which may be aqueous or oil-based. In some aspects, such compositions are prepared as liquid solutions or suspensions, or as solid forms such as tablets, pills, powders and the like. Solid forms suitable for solution in, or suspension in, liquids prior to administration are also contemplated (e.g. lyophilized forms of the compounds), as are emulsified preparations. In some aspects, the liquid formulations are aqueous or oil-based suspensions or solutions. In some aspects, the compounds are mixed with excipients which are pharmaceutically acceptable and compatible with the compounds, e.g. pharmaceutically acceptable salts. Suitable excipients include, for example, water, saline, dextrose, glycerol, ethanol, propylene glycol, polyethylene glycols, and the like, or combinations thereof. In addition, the composition may contain minor amounts of auxiliary substances such as wetting or emulsifying agents, pH buffering agents, preservatives, and the like. If it is desired to administer an oral form of the composition, various thickeners, flavorings, diluents, emulsifiers, dispersing aids or binders and the like are added.

Capsules or tablets may also be enterically coated for the purpose of delaying the release of the formulation contents until reaching the intestine. Such enteric coatings include acrylic and methacrylic esters such as Eudragit® coatings; cellulose ester based coatings such as cellulose acetate phthalate, cellulose acetate, ethylcellulose, carboxymethylcellulose, and microcrystalline cellulose; sodium alginate and alginic acid coatings; polyvinyl alcohol coatings; shellac and shellac derivative-based coatings. Examples of these include Eudragit®, Nutrateric®, C-A-P®, VivaCoat®, NS Enteric®, and others.

"Pharmaceutically acceptable salts" refers to the relatively non-toxic, inorganic and organic acid addition salts, and base addition salts, of compounds of the present invention. These salts can be prepared in situ during the final isolation and purification of the compounds. In particular, acid addition salts can be prepared by separately reacting the purified compound in its free base form with a suitable organic or inorganic acid and isolating the salt thus formed.

Base addition salts can also be prepared by separately reacting the purified compound in its acid form with a suitable organic or inorganic base and isolating the salt thus formed. Base addition salts include pharmaceutically acceptable metal and amine salts. Suitable metal salts include the sodium, potassium, calcium, barium, zinc, magnesium, and aluminum salts. The sodium and potassium salts are preferred. Suitable inorganic base addition salts are prepared from metal bases which include sodium hydride, sodium hydroxide, potassium hydroxide, calcium hydroxide, aluminum hydroxide, lithium hydroxide, magnesium hydroxide, zinc hydroxide and the like. Suitable amine base addition salts are prepared from amines which have sufficient basicity to form a stable salt, and preferably include those amines which are frequently used in medicinal chemistry because of their low toxicity and acceptability for medical use. Ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, piperidine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine, and dicyclohexylamine, and the like. The compounds of the present disclosure include any polymorphs, solvates, and hydrates of the salts described herein.

In a particular embodiment, the subject is an animal. The animal may be selected from the group consisting of humans, non-human primates, cattle, horses, pigs, sheep, goats, dogs, cats, birds, chickens or other poultry, ducks, geese, pheasants, turkeys, quails, guinea pigs, rabbits, hamsters, rats, and mice.

Embodiments of the disclosure also provide methods of preparing or synthesizing compositions as described herein. Exemplary synthesis methods are described in the Example herein.

All percentages disclosed herein are in weight percent, unless otherwise indicated.

Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted to, limit the scope of the invention.

Example

Summary

Oral and parenteral drug delivery systems of paclitaxel (PTX) exhibit serious toxicity due to the presence of high concentration of surfactants (e.g., Cremophor EL, Tween® 80). In order to avoid such issues, the current research work entails the development of a novel self-nanoemulsifying drug delivery system (SNEDDS) containing surfactin, a biosurfactant derived from a microbial source. A preformulation study including solubility analysis indicated suitability of corn oil as the natural lipophile. Nanoemulsion boundaries were delineated by aqueous titration of lipid phase (Ethyl oleate: Plurol® Oleique), Surfactants (Tween® 80 and Surfactin) and cosolvent (Transcutol® HP) to identify the optimum compositions on the basis of formulation quality attributes with globule size <250 nm, emulsification time <3 min and in vitro drug release >85% in 60 min. Biocompatibility evaluation of PTX-Surfactin SNEDDS on rat hepatocytes by $H_2DCF$ assay to determine the ROS level indicated insignificant increase in fluorescence intensity, while PTX Tween® 80-SNEDDS showed nearly 20% increase in ROS levels as compared to the control cells. Further, histopathology examination showed absence of any signs of inflammation from intestinal segments treated with PTX Surfactin-SNEDDS, while PTX Tween® 80-SNEDDS revealed infiltration of cells and presence of inflammation on the intestinal villous microstructures. Anticancer activity evaluation by in vitro cytotoxicity on MCF-7 cells showed PTX Surfactin-SNEDDS and PTX Tween® 80-SNEDDS with $IC_{50}$ of 2.65 µM and 11.52 µM, respectively, while PTX suspension showed $IC_{50}$ of 18.5 µM. Moreover, blank Surfactin-SNEDDS showed $IC_{50}$ of 15.23 µM, while no cytotoxicity was observed for blank Tween® 80-SNEDDS. Overall, the study construed high suitability of biosurfactant for developing the self-nanoemulsifying formulation of PTX with enhanced bioavailability, biocompatibility and synergistic improvement in the anticancer activity over the formulations containing synthetic surfactant.

Materials and Methods

Paclitaxel was generously provided by Cipla Ltd., Mumbai, India, and Surfactin (98% purity; CAS number: 24730-31-2) was purchased from Apollo Biolife, Bhopal, India. Various natural long-chain triglycerides containing lipids like sesame oil, corn oil, jojoba oil, castor oil, safflower oil, olive oil and groundnut oil were purchased form Fisher Scientific Pvt. Ltd., Mumbai, India. Other excipients like Plurol® Oleique, Labrasol, Transcutol® HP, Lauroglycol FCC, Labrafac lipophile WL1349 were received as gift samples from Gattefosse, Mumbai, India. HPLC Zobrax® $C_{18}$ column (4.6 mm×25 cm, 5 µm) used for chromatographic analysis of the drug was purchased from Sigma Aldrich, Mumbai, India. Acetonitrile (HPLC grade), ammonium acetate, formic acid and orthophosphoric acid (analytical reagent grade) were purchased from Fluka Analytical, Mumbai, India. Cell culture nutrient medium like Dulbecco's modified eagle medium (DMEM), fetal bovine serum albumin (FBS) were purchased from Himedia Lab Pvt. Ltd., New Delhi, India. All other chemicals, solvents and reagents used during the studies were of analytical reagent grade and stored under the recommended conditions.

Analytical Method

The analytical method for estimation of the drug (PTX) was performed using the in-house developed high performance liquid chromatographic (HPLC) method. Chromatographic separation was accomplished on Zobrax® $C_{18}$ column (25 cm×4.6 mm, 5 µm) using mobile phase mixture (acetonitrile: water containing 0.1% v/v orthophosphoric acid; 70:30 ratio, pH 3.5), flow rate at 1 mL·min$^{-1}$ and detection at 210 nm. A binary pump RP-HPLC instrument with model Shimadzu LC-10A (M/s Shimadzu, Tokyo, Japan) equipped with mobile phase degasser, heated column thermostat, variable UV/VIS detector SPD-10AVP, column oven and SCL 10AVP system controller was employed for method development and validation studies. Prior to injection of the drug solution, column was equilibrated for at least 30 min with the flow of mobile phase through the system and samples were injected by means of a Rheodyne injector fitted with a 20 µL loop and data acquisition was controlled by Shimadzu Class-VP 5.032 software. The linearity of method was established in the concentration ranging between 10 and 4000 ng·mL$^{-1}$. The method was also validated for accuracy, inter and intraday precision, detection and quantification limit. For bioanalytical estimation in rat plasma, propranolol was used as the internal standard. Method linearity was evaluated by comparing the percent recovery of the drug from standard samples spiked with plasma to that of the blank plasma samples. Liquid-liquid extraction was used for separating PTX from the plasma samples using diethyl ether as extraction solvent. The samples after extraction were filtered through 0.22 µm membrane filter and 10 µL of the sample was injected into the system for chromatographic estimation.

Equilibrium Solubility Evaluation in Lipids and Cosolvents

Solubility evaluation of PTX was carried out in various oils and cosolvents till attaining equilibrium by addition of excess quantity of drug to 1 gm of each of the excipient in culture vials and mixed well using vortex mixer (Remi Instruments, Mumbai, India). The sealed vials were kept on water bath shaker at 37±0.5° C. for 72 h for 150 strokes per minute. After specified time period, the samples were centrifuged at 3,000 rpm (402.5×g) for 15 minutes using a laboratory centrifuge (Remi Instruments, Mumbai, India). Drug was extracted in acetonitrile and supernatant fraction was filtered through 0.45 µm membrane filter, suitably diluted and analyzed by previously developed HPLC method.

Ternary Phase Diagram Construction

The ternary phase diagrams were constructed for evaluating the nanoemulsion region. The oil and solvent with maximal solubility for the drug was selected, and phase titration was study was carried out along with two different surfactants (Tween® 80 and Surfactin). Various ternary mixtures with concentration of oil, surfactant and cosolvent were varied from 5 to 95% (w/w), 40 to 60% (w/w) and 10 to 20% (w/w), respectively. The prepared mixtures were allowed for emulsification in simulated gastric fluid (250 mL) and evaluated for phase clarity and formation of nanoemulsion by measuring transmittance and particle size. Based on the observed values, ternary diagrams were constructed by translating the quantities representing the concentrations of the excipients for portraying the nanoemulsion region.

Preparation and Characterization of PTX-SNEDDS

The nanoemulsion region identified from the ternary phase diagram was used for preparing the PTX-SNEDDS containing two different surfactants. A single oral dose of the drug (5 mg) was dissolved in the lipid and mixed by vortex with gentle heating at 40° C. The surfactant and cosolvent were then added, followed by vortex mixing for 15 min to obtain the SNEDDS preconcentrate. Two types of PTX SNEDDS formulations containing different surfactants such as Tween® 80 and Surfactin were evaluated for various quality attributes viz. emulsification time, phase clarity, globule size and zeta potential.

Characterization of Various SNEDDS

Dispersibility and Emulsification Efficiency

The dispersibility evaluation of SNEDDS was carried out by performing emulsification test. Aliquot (1 g) of formulation was allowed to disperse in the simulated gastric fluid (pH 1.2) followed by stirring at 100 rpm on a magnetic stirrer. The time taken for complete dispersion and emulsification of the formulation to produce the nanoemulsion globules was noted.

Globule Size and Zeta Potential Measurement

The globule size and zeta potential analysis of the SNEDDS was carried out after performing the emulsification test. The dynamic light scattering technique (ZS 90 Malvern Zetasizer) was used and the measurement was performed in triplicate for each formulation.

In Vitro Drug Release Evaluation

The drug release analysis was carried out by filling the SNEDDS in a pretreated dialysis bag (mol. wt. cut-off 12 kDa) using simulated gastric fluid with 0.5% w/v sodium lauryl sulfate (250 mL) for 2 h kept on a magnetic stirring condition at 100 rpm. During the study, the samples (2 mL) were collected at periodic time intervals, followed by replacement with fresh medium. The samples were suitably filtered and HPLC analysis was performed for determining the drug concentration. The amount of drug released and percent drug released was estimated from the initial concentration of the drug in the formulation.

Transmission Electron Microscopy (TEM)

TEM analysis of the optimized SNEDDS was carried out for morphological characterization of the emulsion globules formed after dilution of the SNEDDS in 250 mL SGF. A drop of the diluted sample was placed on copper grid, stained with 1% phosphotungstic acid solution for 30 s, and kept under electron microscope (JEM-2100 F, M/s Jeol, Tokyo, Japan) to visualize the particle morphology.

Biocompatibility and Safety Studies

The biocompatibility and safety of the optimized SNEDDS formulations was evaluated on the rat hepatocytes by in vitro measurement of the intracellular level of Reactive Oxygen Species (ROS) and imaging through confocal laser scanning microscopy (CLSM) analysis. Also, the safety of prepared formulations was evaluated by exposure to the intestinal mucosa, followed by histopathological examination of the intestinal sections. The study protocols were approved from Animal Ethics Committee of Panjab University, Chandigarh, India.

Measurement of ROS Level

The ROS measurement was carried out by exposing the optimized SNEDDS formulations to the freshly extracted rat hepatocytes using 2',7'-dichlorofluorescein ($H_2DCF$) dye method reported in literature. Rat hepatocytes were isolated as per the standard protocol procedure reported in literature [29]. Healthy Wistar rats (150-200 g body weight) were sacrificed by cervical dislocation method. Abdominal hairs were shaved and skin was disinfected with povidone iodine and ethanol solution. A midline incision was made to open the abdomen and liver was carefully dissected out. A cannula was inserted into the portal vein and perfusion solution (PBS, pH 7.4) was slowly infused at a rate of 2 mL/min. After the discoloration of the liver hepatocytes cells from the dark red to pink, it was displaced with the cannula and minced into small pieces by a surgical blade. Further, homogenates were collected and washed with PBS solution (pH 7.4). The homogenate was passed through filter (210 μm×70 μm×40 μm), and the supernatant cell extract was collected, and subjected to centrifugation at 500 rpm (158× g) for 5 min. The pellet containing hepatocytes were suspended in fresh PBS buffer until use. The isolated hepatocytes were observed through light microscope Nikon Eclipse 80i, (Nikon Corp., Chiyoda-ku, Japan). The dye solutions for $H_2DCF$ (10 mM) and DAPI (30 mM) were prepared in DMSO and water, and stored under dark condition to avoid any loss of fluorescence.

Intestinal Histopathology Examination

The biocompatibility of developed formulation was evaluated by histopathological examination of the rat small intestinal segment exposed to optimized SNEDDS formulations. The rats (weighing 150-200 g) were subjected to overnight fasting with free access to water. The animals were randomly divided into three groups with three animals in each group. Rats in two groups were orally administered with optimized blank Tween® 80-SNEDDS and blank Surfactin-SNEDDS, respectively, in the quantity calculated as per the body weight by considering the weight of the optimized formulations for human use, while third group of rats were administered with normal saline only. After 3 h of oral administration, the animals were sacrificed by cervical dislocation and duodenum portion of the small intestine was removed. The intestinal segment was thoroughly washed with the help of Krebs's-Ringer saline solution to clean any debris and stored in 10% formalin solution. The tissue sectioning was carried out by microtomy procedure, and stained with hematoxylin and eosin dye solution. The visual analysis of the tissue section was carried out under light microscope (Nikon S50, Tokyo, Japan) to identify any change in pathophysiology or presence of inflammation in the intestinal microstructure.

Anticancer Activity Evaluation

MTT assay was carried out on MCF-7 cells for evaluating the cytotoxicity of the optimized SNEDDS formulations. For conducting the cytotoxicity assay, the fully grown MCF-7 cells were seeded in 96-well plate ($5 \times 10^4$ cells/well) and incubated for 24 h in $CO_2$ incubator (Thermo Fisher Scientific, Mumbai, India). After the specified time period, the cells were seeded with various treatment formulations viz. PTX suspension, PTX Tween® 80-SNEDDS, PTX Surfactin-SNEDDS, blank Tween® 80-SNEDDS, blank Surfactin-SNEDDS (in five concentrations, i.e., 1, 2, 5, 10 and 20 μM) and control cells without any treatment. After incubation for 24 h, the cells were washed with PBS (pH 7.4). Subsequently, 150 μL of MTT solution (500 mg/mL in PBS) was added to each well and incubated at 37° C. for another 3 h to facilitate formation of formazan crystals. The supernatant fraction was removed and DMSO was added for solubilizing formazan crystals. Thereafter, the dye solution was removed and optical density of the supernatant was measured at 540 nm using ELISA microplate reader (M/s BioTek, Winooski, USA). Based on the results of optical density, the percent inhibition in cell growth was measured by the treatment formulations as per the Eq. (1).

$$\% \text{ Cell growth inhibition} = \frac{\text{Optical } density_{test} - \text{Optical } density_{blank}}{\text{Optical } density_{control} - \text{Optical } density_{blank}} \times 100$$

Statistical Data Analysis

The statistical analysis of data obtained from in vitro and in vivo studies was carried out by ANOVA, followed by post-hoc analysis at 5% level of significance with the help of GraphPad Prism software ver. 6.0 (GraphPad Inc., California, USA).

Results and Discussion

Equilibrium Solubility Analysis

The solubility analysis of PTX was performed in various lipids and solvents Among the lipids studied, the maximal solubility of PTX was observed in 1:1 ratio mixture of ethyl oleate:Plurol® Oleique (198.5 mg·mL$^{-1}$). Among the surfactants and cosolvents, PTX exhibited maximal solubility in Tween® 80 (78 mg·mL$^{-1}$) and Transcutol® HP (235 mg·mL$^{-1}$) which were thus selected for the development of SNEDDS. Also, PTX solubility was evaluated in surfactin as a microbial surfactant selected for preparing the SNEDDS which was found to be 106 mg·mL$^{-1}$. Among the surfactants, PTX showed higher solubility in surfactin as compared to Tween® 80 which provides very good advantage in attaining maximal drug loading efficiency.

Phase Titration Studies

Figure 1B:
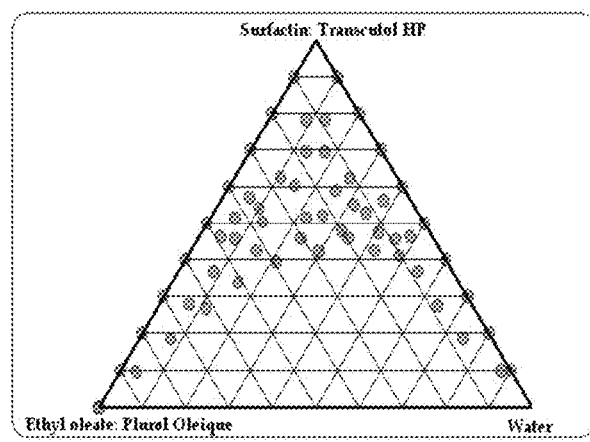

Based on the results of solubility, the phase titration studies were carried out for constructing the ternary phase diagrams. The blends of lipidic and emulsifying agents with maximal solubility were evaluated for the purpose. Aliquot 1 g of the mixtures of lipid (ethyl oleate: Plurol® Oleique) and $S_{mix}$ containing surfactant (Tween® 80/Surfactin) and cosurfactant (Transcutol® HP) mixture in varying ratios from 1:9 to 9:1. Further, the ratio of $S_{mix}$ was kept at 1:1 while the nanoemulsion region obtained was compared. FIG. 1 indicates higher nanomeulsion region for formulation mixtures prepared using Surfactin over the Tween® 80. This could be attributed to the very good emulsification efficiency provided by the functional hydrophilic and lipophilic groups.

Formulation of the PTX-Tween® 80 SNEDDS and PTX-Surfactin SNEDDS

The prototype liquid PTX-SNEDDS were prepared using the lipid, surfactant and cosurfactant ratios which exhibited faster self-emulsification efficiency with adequate phase clarity for formation of nanoemulsion in the ternary phase diagram. A total of seven formulations were prepared by selecting the composition of sesame oil, labrasol and sodium deoxycholate. Table 1 illustrates the formulation composition of the PTX-SNEDDS. The dose of PTX in all the formulations was fixed at 10 mg. The prepared formulations were subjected to extensive characterization studies. Further, the PTX-Cu-SNEDDS was prepared by dissolving desired quantity of curcumin to obtain a homogenous mixture.

TABLE 1

Formulation composition of PTX-SNEDDS

| Formulation ingredients | F1 | F2 | F3 | F4 | F5 | F6 |
|---|---|---|---|---|---|---|
| Paclitaxel (mg) | 5 | 5 | 5 | 5 | 5 | 5 |
| Ethyl oleate: Plurol ® Oleique (%) | 5 | 10 | 13 | 27 | 36 | 40 |
| Tween ® 80/Surfactin (%) | 45 | 55 | 54 | 65 | 57 | 55 |
| Transcutol ® HP (%) | 50 | 35 | 33 | 8 | 5 | 5 |

Characterization of the Prepared SNEDDS
Dispersibility Test and Emulsification Time The dispersibility studies showed faster emulsification of the SNEDDS produced with surfactin with emulsification time within 1 to 3 min in Simulated Gastric Fluid, while SNEDDS produced with Tween® 80 showed emulsification time within 5 to 8 min. The shorter time confirmed faster emulsification efficiency of the prepared SNEDDS, which helps in solubilization of the drug in the gastric milieu. Further, the emulsification efficiency evaluated in other media like, Simulated Intestinal Fluid and Phophate Buffer Solution revealed no significant influence of pH of the medium on it. Apart from these, evaluation of the effect of stirring speed revealed lack of prominent influence on the emulsification time of surfactin SNEDDS, but certainly increased the emulsification time from 3 to 6 min, thus confirming the spontaneous emulsification ability of the surfactin SNEDDS.

Globule Size Measurement

Figure 2:
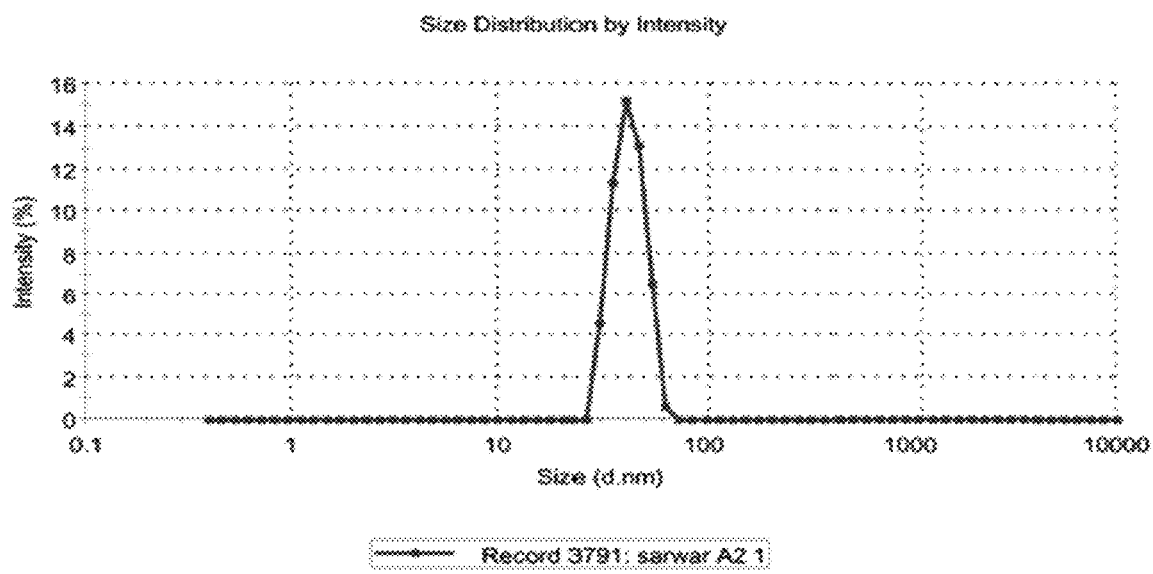
FIG. 2. Particle size distribution profile of PTX-SNEDDS prepared using Tween® 80.
Figure 3:
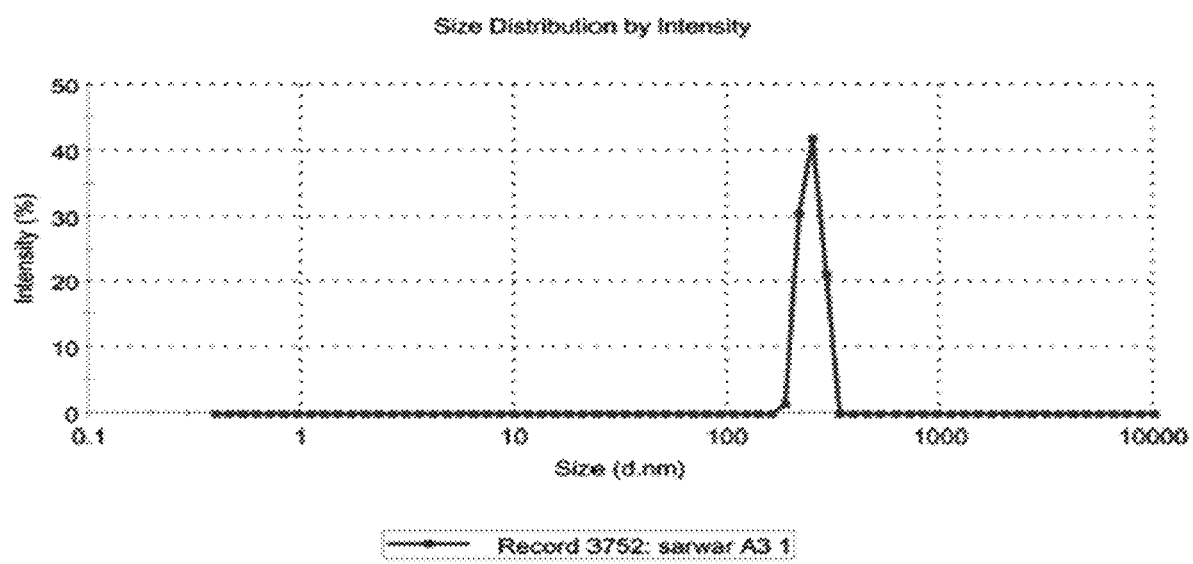
FIG. 3. Particle size distribution profile of PTX-SNEDDS prepared using Surfactin.

The globule size measurement showed SNEDDS with size ranging between 84 and 171 nm, thus confirming the nanostructured nature of the emulsion globules obtained after dilution with SGF. The globule size analysis also showed that at moderately low levels of lipid, intermediate levels of surfactant and low levels of cosurfactant. FIGS. 2 and 3 depict the globule size distribution profile of Tween® 80 and Surfactin SNEDDS with lowest particle size. The globule size was less with surfactin SNEDDS as compared to the SNEDDS containing Tween® 80. This could be attributed to the higher surface interfacial tension lowering properties of surfactin over Tween® 80 to produce the nanoemulsion.

Robustness to Dilution

The dilution studies revealed no signs of cloudiness and/or phase separation for all the prepared SNEDDS after multifold dilution with simulated gastric/intestinal fluids. All the formulations exhibited stable and clear nanoemulsion with absence of precipitation of the drug. Evaluation of the globule size of all the diluted formulations revealed lack of any significant change in the values with increase in the degree of dilution. This corroborated robust nature of the prepared SNEDDS with insignificant influence of multi-fold dilution on the stability.

Thermodynamic Stability Studies

Evaluation of the thermodynamic stability of SNEDDS confirmed lack of any sign(s) of precipitation, creaming or cracking, thereby construing adequate the physiochemical stability of the prepared systems. Also, the studies revealed robustness of the prepared formulations upon spontaneous solubilization in the gastric lumen to form the nanoemulsions.

In Vitro Drug Release Studies

Figure 4:
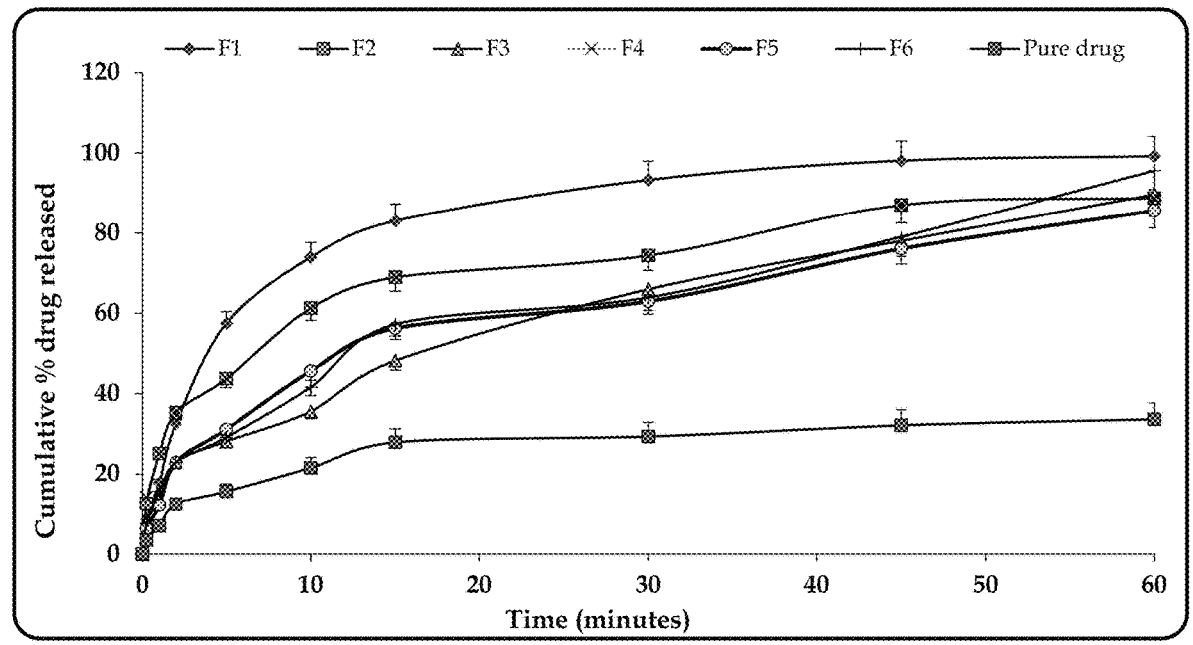
FIG. 4. In vitro drug release profile of PTX from SNEDDS containing Tween® 80 and pure drug; Data expressed as mean±1S.D. (n=6).
Figure 5:
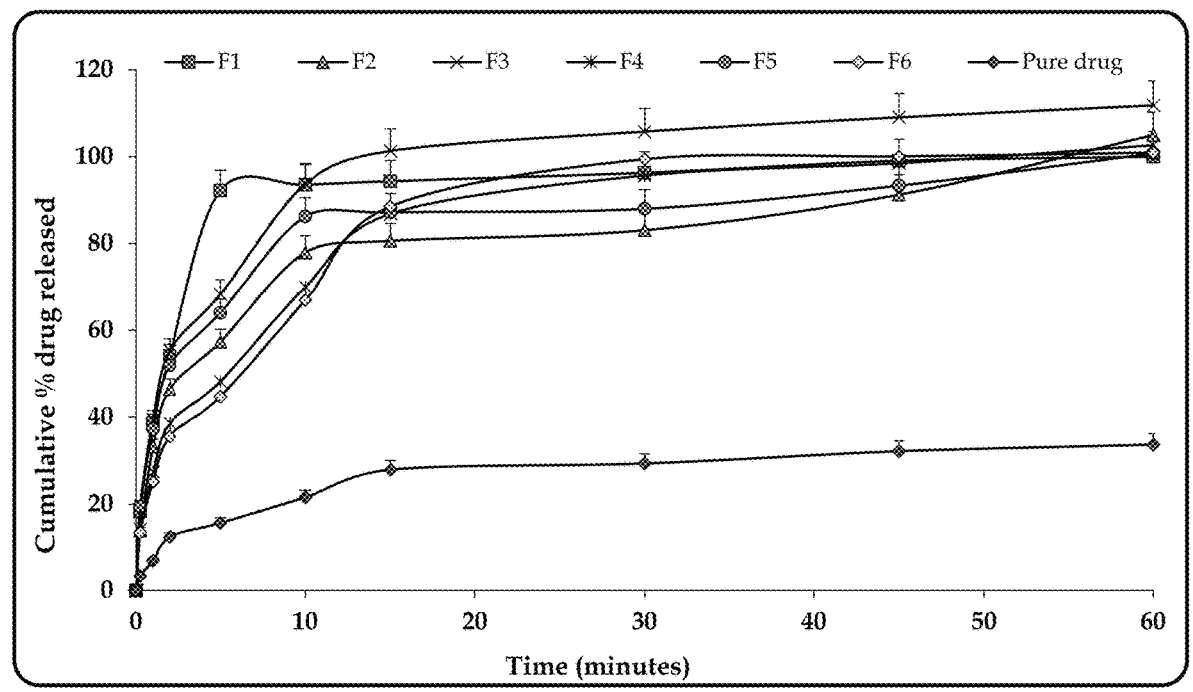
FIG. 5. In vitro drug release profile of PTX from SNEDDS containing Surfactin and pure drug; Data expressed as mean±1S.D. (n=6).

In vitro dissolution studies revealed that SNEDDS loaded with PTX showed more than 85% drug release within 30 min and almost complete drug release within 1 h from SNEDDS prepared using Tween® 80 and Surfactin, respectively (FIGS. 4 and 5). This indicated faster drug release characteristics of PTX from SNEDDS formulation ostensibly attributed to the judicious selection of the lipidic and emulsifying excipients, which facilitate complete solubilization of the drug in the dissolution medium by micellar solubilization mechanism [30]. Surfactin SNEDDS revealed higher and faster drug release possibly due to faster emulsification efficiency and smaller globule size. Overall, the release studies revealed a net 3.24-fold improvement in the drug release rate for both the drugs from SNEDDS vis-à-vis the pure drug suspension.

Selection of the Optimized Formulation

Figure 6A:
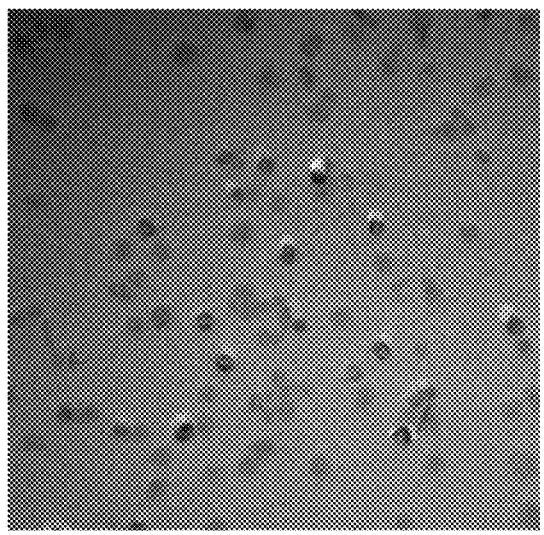
FIGS. 6A-B. Particle size of SNEDDS prepared using (A) Tween® 80 and (B) Surfactin.
Figure 6B:
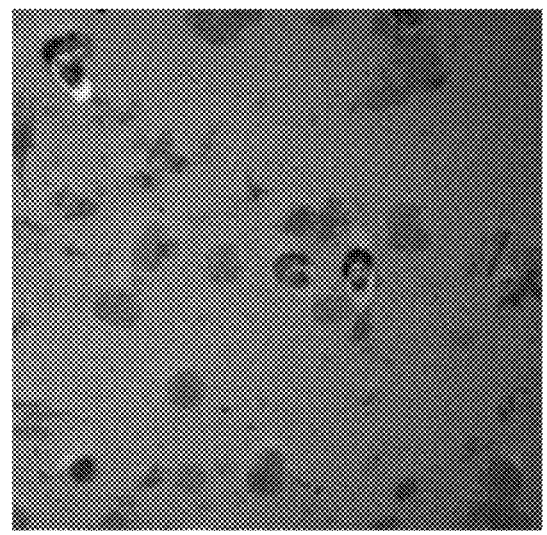

The optimized PTX-SNEDDS was selected based on the criteria like faster self-emulsification efficiency, smaller globule size, thermodynamic stability and faster drug release. Among the various prepared formulations, the PTX-SNEDDS in F2 showed optimal biopharmaceutical characteristics, thus chosen as the optimized formulation. Characterization of the optimized formulation using TEM revealed the formation of very fine emulsion globules (FIG. 6).

Biocompatibility and Safety Studies

The biocompatibility study was performed by conducting H2DCF dye assay for determining the ROS levels expressed in the rat hepatocytes and subsequently safety evaluation by histopathological evaluation indicated excellent outcomes pertaining to PTX Surfactin-SNEDDS over the PTX Tween® 80-SNEDDS.

Measurement of ROS Level

Figure 7:
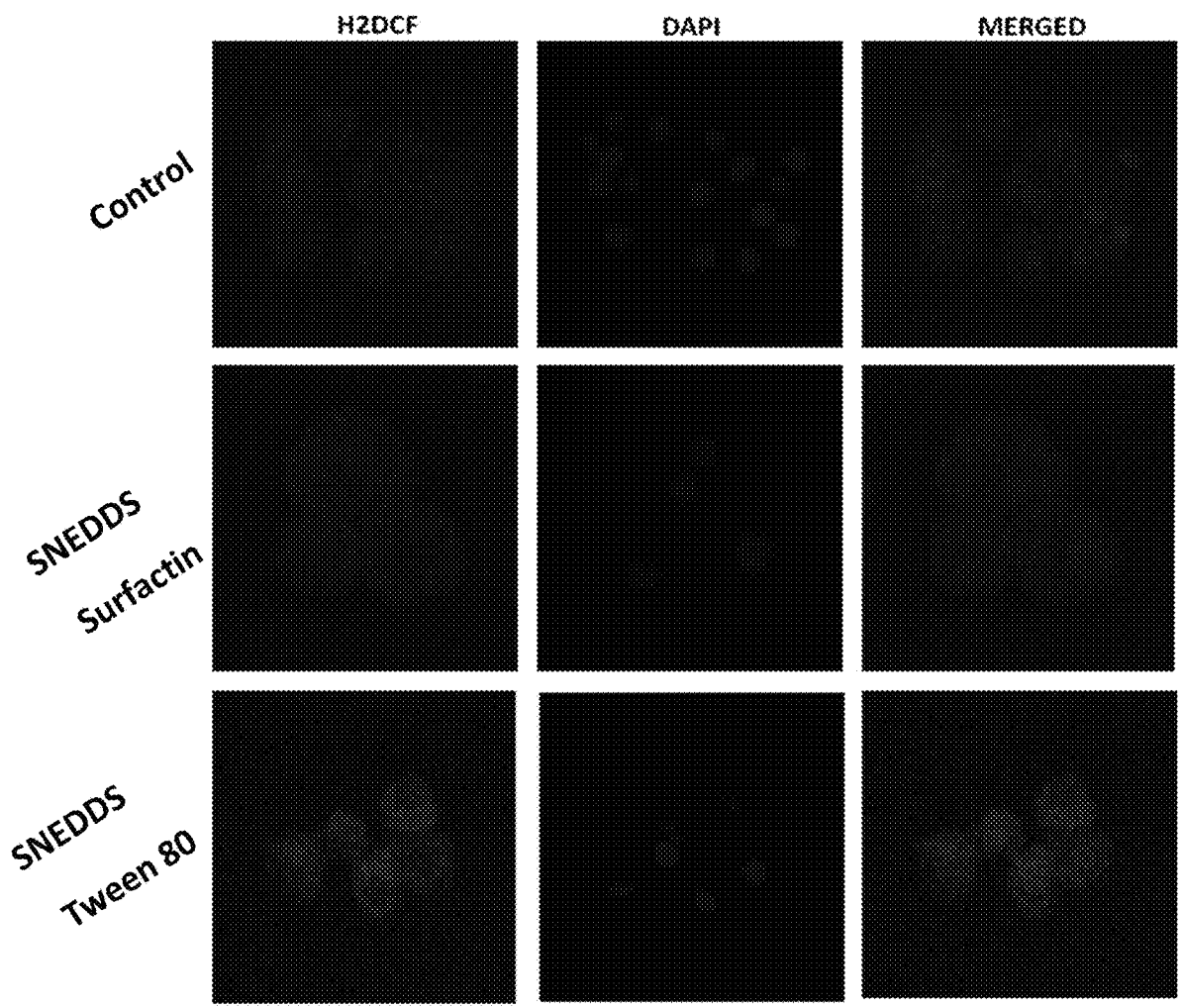
FIG. 7. CLSM images of rat hepatocytes (Control), and after treatment with SNEDDS prepared with Surfactin and Tween® 80, indicating fluorescence produced by $H_2DCF$ as a function of ROS.
Figure 8:
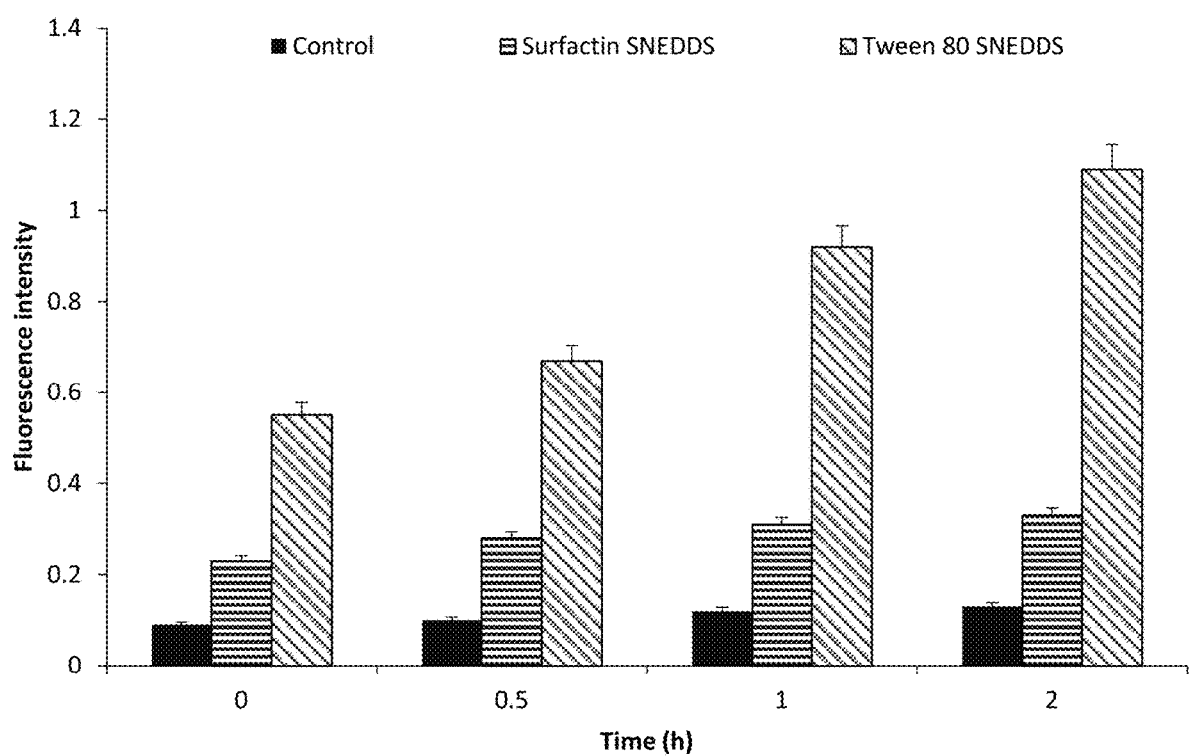
FIG. 8. Fluorescence intensity observed with the rat hepatocytes (control cells), and the cells treated with Surfactin SNEDDS and Tween® 80 SNEDDS. Data expressed as mean±1SD (n=3).

The measurement of ROS was performed with the help of CLSM, where the green fluorescence produced by the H2DCF dye after reaction with cellular ROS (i.e., rat hepatocytes) was measured for different formulations. FIG. 7 illustrates the CLSM images of the rat hepatocytes after treatment with blank surfactin SNEDDS and blank Tween® 80 SNEDDS with fluorescence of intensity indicating the levels of ROS generated. Further, the study also provided the time-dependent data for the fluorescence generated with the rat hepatocytes upon exposure to the treatment (SNEDDS) formulations. As indicated in FIG. 8, the rat hepatocytes treated with SNEDDS prepared with Surfactin showed very minimal generation of ROS levels as compared to the hepatocytes exposed to the SNEDDS containing Tween® 80 vis-à-vis the fluorescence intensity indicating ROS level generated with the control cells. Further, the results indicated time-dependent increase in fluorescence intensity up to 2 h, followed by a declining phase (data not shown).

Intestinal Histopathological Examination

Histopathological examination of the rat intestine after exposure to the SNEDDS prepared with Surfactin and Tween® 80 showed good biocompatibility. FIG. 9 illustrates the histopathology images of the small intestine segments as the control and the rat intestines exposed to various treatment formulations. SNEDDS containing Surfactin in the formulation indicated no visible changes in the intestinal histopathology as compared to the control, while SNEDDS containing Tween® 80 showed minor signs of inflammation of the intestinal segment. The studies compared the biocompatible nature of the surfactin SNEDDS over the Tween® 80 SNEDDS.

Anticancer Activity Evaluation

In vitro anticancer activity of the blank SNEDDS, PTX Tween® 80-SNEDDS, PTX Surfactin-SNEDDS, and PTX-suspension was evaluated. PTX Surfactin-SNEDDS and PTX Tween® 80-SNEDDS had an $IC_{50}$ of 2.65 µM and 11.52 µM, respectively, while PTX suspension showed an $IC_{50}$ of 18.5 µM. Moreover, blank Surfactin-SNEDDS showed $IC_{50}$ of 15.23 µM, while no cytotoxicity was observed for blank Tween® 80-SNEDDS. This confirmed superior anticancer activity of the PTX Surfactin-SNEDDS over the PTX Tween® 80-SNEDDS. Besides, the cytotoxicity observed from the blank surfactin SNEDDS revealed interesting observation on positive influence of blank formulation on the MCF-7 cells which was not observed in case of blank Tween® 80 SNEDD formulation. This study revealed higher cytotoxic potential of the PTX surfactin SNEDDS which could be attributed to the synergistic potential of surfactin and PTX for providing higher cytotoxicity over the PTX Tween® 80 SNEDDS.

CONCLUSIONS

This Example described the successful development of SNEDDS formulation using a microbial surfactant which exhibited higher cytotoxic activity and improved bioavailability of the investigated drug, paclitaxel. The use of microbial surfactant in the formulation further revealed no toxicity and high biocompatibility over the SNEDDS prepared using Tween® 80. The findings observed from this work provide a safe and effective bio enhanced oral formulation of the drug for the treatment of cancer.

Acknowledgment

This project was funded by Knowledge Economy & Technology Transfer Center, King Abdulaziz University, Jeddah, Saudi Arabia. Grant number 2020-050.

REFERENCES

1. Thanki, K., et al., *Oral delivery of anticancer drugs: Challenges and opportunities. Journal of Controlled Release*, 2013. 170(1): p. 15-40.
2. Nayak, A. K., et al., *Drug delivery: present, past, and future of medicine, in Applications of Nanocomposite Materials in Drug Delivery*, Innamuddin, A. Asiri, and A. Mohammad, Editors. 2018, Academic Press: New York. p. 255-282.
3. Rahman, M. and S. Beg, *Hitting the target-refining anticancer nanomedicine development*. European Pharmaceutical Review, 2019. 24(4): p. 14-16.
4. Swain, S., et al., *Nanoparticles for Cancer Targeting: Current and Future Directions*. Curr Drug Deliv, 2016. 13(8): p. 1290-1302.
5. Sparreboom, A., et al., *Limited oral bioavailability and active epithelial excretion of paclitaxel (Taxol) caused by P-glycoprotein in the intestine*. Proceedings of the National Academy of Sciences of the United States of America, 1997. 94(5): p. 2031-2035.
6. Sandhu, P. S., et al., *Novel dietary lipid-based self-nanoemulsifying drug delivery systems of paclitaxel with p-gp inhibitor: implications on cytotoxicity and biopharmaceutical performance*. Expert Opinion on Drug Delivery, 2015. 12(11): p. 1809-1822.
7. Beg, S., et al., *QbD-Based Development of Cationic Self-nanoemulsifying Drug Delivery Systems of Paclitaxel with Improved Biopharmaceutical Attributes*. AAPS PharmSciTech, 2019. 20(3): p. 118.
8. Harshita, et al., *Paclitaxel-loaded Nanolipidic Carriers with Improved Oral Bioavailability and Anticancer Activity against Human Liver Carcinoma*. AAPS PharmSciTech, 2019. 20(2): p. 87.
9. Zhao X, et al., *Chronic chemotherapy with paclitaxel nanoparticles induced apoptosis in lung cancer in vitro and in vivo*. Int J Nanomedicine, 2019. 14: p. 1299-1309.
10. Lei, M., et al., *Co-delivery of paclitaxel and gemcitabine via a self-assembling nanoparticle for targeted treatment of breast cancer*. RSC Advances, 2019. 9(10): p. 5512-5520.
11. Wu, C., et al., *Pure paclitaxel nanoparticles: preparation, characterization, and antitumor effect for human liver cancer SMMC-7721 cells*. International journal of nanomedicine, 2018. 13: p. 6189-6198.
12. Ma, P. and R. J. Mumper, *Paclitaxel Nano-Delivery Systems: A Comprehensive Review*. Journal of nanomedicine & nanotechnology, 2013. 4(2): p. 1000164-1000164.
13. Harshita, et al., *Nanopaclitaxel therapy: an evidence based review on the battle for next-generation formulation challenges*. Nanomedicine, 2019. 14(10): p. 1323-1341.
14. B Singh, S. B., S Beg, O P Katare, *Handling Poorly Bioavailable Drugs Using Nanoemulsifying Drug Delivery Systems*. The Pharma Review, 2011: p. 91-98.
15. Singh, B., et al., *Recent Advances in Self-Emulsifying Drug Delivery Systems (SEDDS)*. Critical Reviews™ in Therapeutic Drug Carrier Systems, 2014. 31(2): p. 121-185.
16. Hussain, A., et al., *Self-emulsifying systems for oral bioavailability enhancement*. Recent Patents on Nanomedicine 2015. 5(2): p. 71-77.
17. Beg, S. and A. Samad, *Lipid-Based Nanostructured Drug Delivery Systems with Improved Biopharmaceutical Attributes*. Recent Patents on Nanomedicine 2015. 5(2): p. 70-70.
18. Cho, H. Y., et al., *Self-Emulsifying Drug Delivery System for Enhancing Bioavailability and Lymphatic Delivery of Tacrolimus*. J Nanosci Nanotechnol, 2015. 15(2): p. 1831-1841.
19. Rodrigues, L. g., et al., *Biosurfactants: potential applications in medicine*. Journal of Antimicrobial Chemotherapy, 2006. 57(4): p. 609-618.

20. Gudiña, E. J., et al., *Potential therapeutic applications of biosurfactants*. Trends Pharmacol Sci, 2013. 34(12): p. 667-675.
21. Fracchia, L., et al., *Biosurfactants and Bioemulsifiers: Biomedical and Related Applications—Present Status and Future Potentials*, in Biomedical Science, Engineering and Technology, D. N. Ghista, Editor. 2012, inTech Open. p. 325-370.
22. Kural, F. H. and R. H. Gursoy, *Formulation and Characterization of Surfactin-Containing Self-Microemulsifying Drug Delivery Systems (SF-SMEDDS)*. Hacettepe University Journal of the Faculty of Pharmacy, 2010. 30(2): p. 171-186.
23. Huang W, et al., *Surfactin-based nanoparticles loaded with doxorubicin to overcome multidrug resistance in cancers*. Int J Nanomedicine, 2018. 13: p. 1723-1736.
24. Ohadi, M., et al., *Potential Use of Microbial Surfactant in Microemulsion Drug Delivery System: A Systematic Review*. Drug design, development and therapy, 2020. 14: p. 541-550.
25. Gursoy, N., et al., *Excipient effects on <em> in vitro</em> cytotoxicity of a novel paclitaxel self‐ emulsifying drug delivery system*. Journal of Pharmaceutical Sciences, 2003. 92(12): p. 2411-2418.
26. Gao, P., et al., *Development of a supersaturable SEDDS (S‐ SEDDS) formulation of paclitaxel with improved oral bioavailability*. Journal of Pharmaceutical Sciences, 2003. 92(12): p. 2386-2398.
27. Lo, J.-T., et al., *Self-emulsifying O/W formulations of paclitaxel prepared from mixed nonionic surfactants*. Journal of Pharmaceutical Sciences, 2020. 99(5): p. 2320-2332.
28. Zhang, X. N., et al., *An alternative paclitaxel self-emulsifying microemulsion formulation: preparation, pharmacokinetic profile, and hypersensitivity evaluation*. PDA J Pharm Sci Technol, 2006. 60(2): p. 89-94.
29. Owusu-Ansah, E., A. Yavari, and U. Banerjee, *A protocol for in vivo detection of reactive oxygen species*. Protocol Exchange, 2008: p. [Epub ahead of print].
30. Beg, S., et al., *Development of solid self-nanoemulsifying granules (SSNEGs) of ondansetron hydrochloride with enhanced bioavailability potential*. Colloids Surf B Biointerfaces, 2013. 101: p. 414-23.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

What is claimed is:

1. A self-nanoemulsifying drug delivery system (SNEDDS) composition comprising:
   at least one chemotherapeutic compound, wherein the at least one chemotherapeutic compound is selected from the group consisting of abeotaxane, paclitaxel, oraxol, and docetaxel or a pharmaceutically acceptable salt thereof or mixture thereof;
   at least one biocompatible surfactant, wherein the at least one biocompatible surfactant includes surfactin; and
   at least one co-surfactant.

2. The composition of claim 1, wherein the at least one chemotherapeutic compound is paclitaxel.

3. The composition of claim 1, wherein the composition comprises 45-65 wt % surfactin.

4. The composition of claim 1, wherein the at least one co-surfactant is selected from the group consisting of ethyl oleate, polyglyceryl-3 dioleate, and 2-(2-ethoxyethoxy)ethanol.

5. The composition of claim 4, wherein the co-surfactant includes
   1-10 wt % ethyl oleate;
   1-10 wt % polyglyceryl-3 dioleate; and
   30-40 wt % 2-(2-ethoxyethoxy)ethanol.

6. The composition of claim 4, wherein the at least one co-surfactant includes ethyl oleate and polyglyceryl-3 dioleate at a 1:1 molar ratio.

7. The composition of claim 1, wherein the composition does not contain polyethoxylated castor oil.

8. The composition of claim 1, wherein the composition does not contain polyoxyethylene sorbitan monooleate.

9. A method of enhancing the bioavailability of a chemotherapeutic compound in a subject, comprising orally administering an effective amount of the composition of claim 1 to the subject.

10. A method of treating cancer in a subject in need thereof, comprising administering an effective amount of the composition of claim 1 to the subject.

\* \* \* \* \*

UNITED STATES PATENT AND TRADEMARK OFFICE
CERTIFICATE OF CORRECTION

| | | |
|---|---|---|
| PATENT NO. | : 11,547,690 B1 | Page 1 of 1 |
| APPLICATION NO. | : 17/851399 | |
| DATED | : January 10, 2023 | |
| INVENTOR(S) | : Kazmi et al. | |

It is certified that error appears in the above-identified patent and that said Letters Patent is hereby corrected as shown below:

On the Title Page

The inventors addresses should be corrected as follows:
Imran Kazmi, Jeddah (SA); Sarwar Beg, New Delhi (IN); Mahfoozur Rahman, Allahabad (IN); Fahad A. Al-Abbasi, Jeddah (SA); Muhammad Afzal, Sakaka (SA); Hisham N. Altayb, Jeddah (SA)

Signed and Sealed this
Twenty-eighth Day of March, 2023

*Katherine Kelly Vidal*

Katherine Kelly Vidal
*Director of the United States Patent and Trademark Office*